United States Patent [19]

Yabe et al.

[11] Patent Number: 5,354,770

[45] Date of Patent: Oct. 11, 1994

[54] USING IMIDAZOLYL TETRAHYDRONAPHTHALENE CARBOXYLIC ACIDS TO INHIBIT RESTENOSIS

[75] Inventors: Yoshimasa Yabe, Tokyo; Tomoyoshi Suzuki, Osaka; Tomoo Shiozawa, Tokyo, all of Japan

[73] Assignee: Daiichi Pharmaceutical Co., Ltd., Tokyo, Japan

[21] Appl. No.: 15,674

[22] Filed: Feb. 9, 1993

Related U.S. Application Data

[63] Continuation of Ser. No. 703,714, May 21, 1991, abandoned, which is a continuation of Ser. No. 485,716, Feb. 27, 1990, abandoned.

[30] Foreign Application Priority Data

Feb. 27, 1989 [JP] Japan ................... 1-46093

[51] Int. Cl.$^5$ ........................................... A61K 31/415
[52] U.S. Cl. .................... 514/399; 514/396; 514/400; 514/822
[58] Field of Search ................ 514/396, 399, 400, 822

[56] References Cited

U.S. PATENT DOCUMENTS

| | | | |
|---|---|---|---|
| 4,665,188 | 5/1987 | Kanao | 548/341 |
| 4,777,257 | 10/1988 | Kanao | 546/342 |
| 4,929,602 | 5/1990 | Harker et al. | 514/18 |
| 4,955,878 | 9/1990 | See et al. | 604/181 |

FOREIGN PATENT DOCUMENTS 0297593 1/1989 European Pat. Off. .

OTHER PUBLICATIONS

Patent Abstracts of Japan, vol. 11, No. 13 (C-397)[2460], Jan. 14, 1987.

R. Moroi et al., "Improvement in ischemic myocardial metabolism by 6-(1-imidazolylmethyl)-5,6,7,8-tetrahydro-naphthalene-2-carboxylic acid hydrocholoride hemihydrate(DP-1904), a thromboxane A2 synthetase inhibitor, on the isolated guinea-pig heart as studied by 31P NMR", Journal of Pharmaceutical Science, vol. 76, No. 11, Nov. 1987, p. 164, abstract No. H06-W-05.

Liu et al., "Restenosis After Coronary Angioplasty—Potential Biologic Determinants and Role of Intimal Hyperplasia," vol. 79, No. 6 (Jun. 1989).

Mickelson, JK American Heart Journal 113(6):1345-1352 (1987).

Cox, Jafna L. Canadian J. Cardiology 4(4):201-210 (1988).

Primary Examiner—Gary E. Hollinden
Attorney, Agent, or Firm—Sughrue, Mion, Zinn, Macpeak & Seas

[57] ABSTRACT

A restenosis inhibiting agent for the treatment or prevention of restenosis after percutaneous transluminal coronary angioplasty which comprises a pharmaceutically effective amount of a compound of the following general formula or a pharmaceutically acceptable salt thereof as an active ingredient:

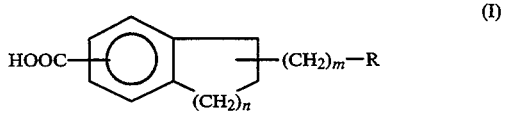

(I)

wherein R is an imidazolyl group, a thiazolyl group or a pyridyl group, n is an integer of 1 or 2, and m is an integer of 1 to 4.

4 Claims, No Drawings

USING IMIDAZOLYL TETRAHYDRONAPHTHALENE CARBOXYLIC ACIDS TO INHIBIT RESTENOSIS

This is a continuation of application Ser. No. 07/703,714 filed May 21, 1991 abandoned, which is a continuation of application Ser. No. 07/485,716 filed Feb. 27, 1990 abandoned.

FIELD OF THE INVENTION

The present invention relates to a post-angioplasty restenosis inhibiting agent. More particularly, the invention relates to a restenosis inhibiting agent for the treatment or prevention of restenosis after percutaneous transluminal coronary angioplasty.

BACKGROUND OF THE INVENTION

Percutaneous transluminal coronary angioplasty (hereinafter, referred to briefly as PTCA) is a relatively new approach to the treatment of ischemic heart diseases and technically involves mechanical dilatation of the stenosed region of the coronary artery by means of a balloon. However, it is known that PTCA is not a radical therapy for atherosclerotic lesions of the coronary arteries, and the mechanically dilated part of the coronary arteries undergoes restenosis within several post-angioplasty months with a frequency of about 40 percent. For controlling this restenosis, antiplatelets, anticoagulants, etc. have heretofore been tried, but drugs that would be sufficiently effective clinically are not available as yet.

SUMMARY OF THE INVENTION

As a result of an extensive investigation to obtain a compound having an excellent inhibitory effect on post-PTCA restenosis, the inventors of the present invention found that a compound of the following general formula or a pharmaceutically acceptable salt thereof:

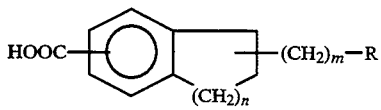
(I)

wherein R is a an imidazolyl group, a thiazolyl group or a pyridyl group, n is an integer of 1 or 2, and m is an integer of 1 to 4, is effective in inhibiting post-PTCA restenosis of the coronary artery, and have completed the present invention.

The above-mentioned compound of general formula (I) and salt thereof are known to inhibitors of thromboxane $A_2$ synthesis, and are effective in ischemic heart disease as disclosed in U.S. Pat. Nos. 4,665,188 and 4,777,257. However, it is a novel finding that these compounds have an inhibitory effect on post-PTCA restenosis.

The present invention is therefore directed to a post-PTCA restenosis inhibiting agent comprising a pharmaceutically effective amount of a compound of the general formula (I) or a pharmaceutically acceptable salt thereof as an active ingredient.

DETAILED DESCRIPTION OF THE INVENTION

The post-PTCA restenosis inhibiting agent of the invention comprises, as aforesaid, a compound of general formula (I) or a pharmaceutically acceptable salt thereof as an active ingredient. The salt is any of pharmaceutically acceptable salts, for example, acid addition salts with inorganic acids such as hydrochloric acid, sulfuric acid, nitric acid, etc., or organic acids such as fumaric acid, tartaric acid, maleic acid, succinic acid, etc., and salts, involving the carboxyl group thereof, with alkali metals such as sodium, potassium, etc. or alkaline earth metals such as calcium, magnesium and so on. In the compound of the formula (I), 6-(1-indazolyl-methyl)-5,6,7,8-tetrahydronaphthalene-2-carboxylic acid and salts thereof are preferred.

The safety of the compound (I), inclusive of salts thereof, has been established in an acute toxicity study in which the compound (I) or a salt thereof was administered orally to rats and its $LD_{50}$ value determined.

The compound (I) or the salt thereof can be processed into various dosage forms by the established pharmaceutical procedures using known excipients, diluents and/or carriers, such as lactose, corn starch, hydroxypropyl cellulose, magnesium stearate and the resulting preparations, which may be tablets, powders, capsules, injections, etc., can be administered, for example, by the oral, subcutaneous, intramuscular or intravenous route.

The oral dosage, for instance, of the compound (I) or salt thereof is generally in the range of 100 to 1,000 mg/day for an adult human.

It has been confirmed clinically that the compound (I) and the salts thereof have an excellent inhibitory effect on post-PTCA restenosis. Therefore, the post-PTCA restenosis inhibiting agent of the present invention is useful in the treatment or prevention of post-PTCA restenosis.

The present invention is now illustrated in greater detail by the following examples but it should be understood that the present invention is not limited thereto.

EXAMPLE 1

In 18 patients with angina pectoris in whom elective PTCA was indicated, 6-(1-imidazolylmethyl)- 5,6,7,8-tetrahydronaphthalene-2-carboxylic acid hydrochloride hemihydrate (hereinafter, referred to as Compound A) was administered orally in a dose of 200 mg three times a day after each meal (600 mg/day) pre-angioplasty, beginning about three days before PTCA, and post-angioplasty for 3 months (treated group). Coronary angiography was performed before, immediately after, and 3 months after PTCA. Based on the coronary angiographic findings, inhibition of restenosis of the right coronary artery, left anterior descending artery and left circumflex artery was evaluated, by site of lesion, according to the criteria in Table 1 shown below. Further, based on the results of the evaluation, overall efficacy evaluation by individual patient was made.

TABLE 1

Criteria for evaluation of coronary angiographic findings

In regard to luminal diameter:
1. Excellent post-angioplasty course: unchanged or expanded
2. Good post-angioplasty course: a decrease in luminal diameter of less than 50%
3. Poor post-angioplasty course: a decrease in luminal diameter of 50% or more and less than 100%

4. Worse post-angioplasty course: a decrease in luminal diameter of 100% or progression of stenosis as compared with pre-PTCA condition As controls (control group), placebo was similarly administered to 15 patients with angina pectoris in whom effective PTCA was indicated and coronary angiography was performed before and after PTCA.

In both of the treated and control groups, calcium antagonists, viz. nifedipine and diltiazem, antianginal drugs, viz. ISDN and nicorandil, and antiarteriosclerotic agents, viz. elastase, etc. were used concurrently as necessary as shown in Table 2 below. However, there was no significant difference ($X^2$ test) between the two groups in the use of concomitant drugs, as in other patient characteristics.

TABLE 2

| Concomitant Drug | Control Group | Treated Group | Test |
|---|---|---|---|
| Nifedipine | 14 | 15 | |
| Diltiazem | 1 | 1 | |
| ISDN | 15 | 18 | |
| Nicorandil | 3 | 7 | Not significant |
| Elastase | 5 | 0 | |
| Others | 4 | 4 | |

The results are shown in Tables 3 and 4 below.

TABLE 3

Evaluation of coronary angiographic findings - by site of lesion -

| Site | | Number of Lesions | Excellent | Good | Poor | Worse |
|---|---|---|---|---|---|---|
| Right Coronary Artery | Control group | 5 | 2 | 0 | 3 | 0 |
| | Treated group | 8 | 3 | 4 | 0 | 1 |
| Left Anterior Descending Artery | Control group | 20 | 3 | 9 | 5 | 3 |
| | Treated group | 9 | 4 | 3 | 1 | 1 |
| Left Circumflex Artery | Control group | 1 | 0 | 1 | 0 | 0 |
| | Treated group | 11 | 2 | 7 | 1 | 1 |
| (Note) Total | Control group | 26 | 5 (19.2%) | 10 (57.7%) | 8 | 3 |
| | Treated group | 28 | 9 (32.1%) | 14 (82.1%) | 2 | 3 |

(%): Cumulative %
Note: Wilcoxon test
P = 0.100

TABLE 4

Overall Efficacy Evaluation, by Individual Patient (based on coronary angiographic findings)

| | Excellent | Good | Poor | Worse | Number of Patients |
|---|---|---|---|---|---|
| Control group | 0 | 7 | 5 | 3 | 15 |
| Treated group | 7 (38.9%) | 7 (46.7%) (77.8%) | 3 | 1 | 18 |

(%): Cumulative %
Wilcoxon test
P = 0.010
Fisher test (with regard to excellent ratings)
P = 0.009

As clearly seen from the above tables, it was clinically confirmed that in both evaluations by lesion and by patient, a superior inhibitory effect on post-PTCA restenosis was obtained in the treated group than in the control group.

EXAMPLE 2

The $LD_{50}$ values of Compound A by probit method are shown in Table 5 below.

TABLE 5

| $LD_{50}$ values (rats, per oral) | |
|---|---|
| $LD_{50}$ (mg/kg) | |
| Male | Female |
| 2438 | 1994 |

While the invention has been described in detail and with reference to specific embodiments thereof, it will be apparent to one skilled in the art that various changes and modifications can be made therein without departing from the spirit and scope thereof.

What is claimed is:

1. A method for the treatment or prevention of restenosis after percutaneous transluminal coronary angioplasty which comprises administering to a host about to undergo and/or having just undergone percutaneous transluminal coronary angioplasty a compound of formula (I) or a pharmaceutically acceptable salt thereof as an active ingredient:

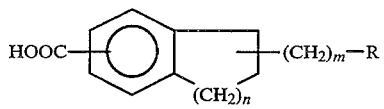

(I)

wherein R is an imidazolyl group, n is an integer of 1 or 2, and m is an integer of 1 to 4, in an amount effective to treat or prevent restenosis after percutaneous transluminal coronary angioplasty.

2. The method of claim 1, wherein said compound is 6-(1-imidazolylmethyl)-5,6,7,8-tetrahydronaphthalene-2-carboxylic acid.

3. The method of claim 1, wherein said pharmaceutically acceptable salt is 6-(1-imidazolylmethyl)-5,6,7,8-tetrahydronaphthalene-2-carboxylic acid hydrochloride hemihydrate.

4. The method of claim 1, wherein said active ingredient is orally administered to said host in an amount of from 100 to 1000 mg per day.

* * * * *